United States Patent
Baek et al.

(10) Patent No.: US 9,517,997 B2
(45) Date of Patent: Dec. 13, 2016

(54) PROCESS FOR CONTINUOUS RECOVERING (METH)ACRYLIC ACID AND APPARATUS FOR THE PROCESS

(71) Applicant: LG CHEM, LTD., Seoul (KR)

(72) Inventors: Se-Won Baek, Daejeon (KR); Jong-Hun Song, Daejeon (KR); Sul-Hee Yoo, Daejeon (KR)

(73) Assignee: LG Chem, Ltd., Seoul (KR)

( * ) Notice: Subject to any disclaimer, the term of this patent is extended or adjusted under 35 U.S.C. 154(b) by 133 days.

(21) Appl. No.: 14/415,113

(22) PCT Filed: Jul. 9, 2013

(86) PCT No.: PCT/KR2013/006101
§ 371 (c)(1),
(2) Date: Jan. 15, 2015

(87) PCT Pub. No.: WO2014/021560
PCT Pub. Date: Feb. 6, 2014

(65) Prior Publication Data
US 2015/0203431 A1  Jul. 23, 2015

(30) Foreign Application Priority Data

Aug. 3, 2012 (KR) .................. 10-2012-0085339
Jul. 9, 2013 (KR) .................. 10-2013-0080189

(51) Int. Cl.
| C07C 51/46 | (2006.01) |
| C07C 51/43 | (2006.01) |
| C07C 51/44 | (2006.01) |
| C07C 51/48 | (2006.01) |
| B01D 53/14 | (2006.01) |
| B01D 11/04 | (2006.01) |

(52) U.S. Cl.
CPC ............ *C07C 51/46* (2013.01); *B01D 11/043* (2013.01); *B01D 53/1487* (2013.01); *C07C 51/43* (2013.01); *C07C 51/44* (2013.01); *C07C 51/48* (2013.01); *B01D 2252/103* (2013.01); *B01D 2257/70* (2013.01); *Y02P 20/51* (2015.11)

(58) Field of Classification Search
CPC .. C07C 51/46; B01D 53/1418; B01D 53/1456
See application file for complete search history.

(56) References Cited

U.S. PATENT DOCUMENTS

| 3,553,261 | A | * | 1/1971 | Sennewald et al. .... C07C 51/48 203/60 |
| 4,166,774 | A | * | 9/1979 | Wagner .................. C07C 51/48 203/16 |
| 6,084,127 | A | | 7/2000 | Sakamoto et al. |
| 6,448,438 | B1 | * | 9/2002 | Yada ....................... C07C 51/44 562/532 |

FOREIGN PATENT DOCUMENTS

| CN | 1247186 | 3/2000 |
| CN | 101835736 | 9/2010 |
| JP | 2002128728 | 5/2002 |
| JP | 2009242285 | 10/2009 |
| KR | 1019810001298 | 10/1981 |
| KR | 1019990045320 | 6/1999 |
| KR | 100375780 | 8/2003 |
| KR | 1020050016815 | 2/2005 |
| KR | 100584677 | 5/2006 |
| KR | 1020090041355 | 4/2009 |
| KR | 101011769 | 2/2011 |

* cited by examiner

Primary Examiner — Paul A Zucker
(74) Attorney, Agent, or Firm — Dentons US LLP

(57) ABSTRACT

This disclosure relates to a method of continuous recovery of (meth)acrylic acid and an apparatus used for the continuous recovery method. The continuous recovery method of (meth)acrylic acid according to the present invention may maintain a recovery rate of (meth)acrylic acid equivalent to that of the previous recovery method, and yet may significantly reduce energy consumption, and may minimize polymerization of (meth)acrylic acid in the recovery process, thus providing more improved operation stability.

18 Claims, 1 Drawing Sheet

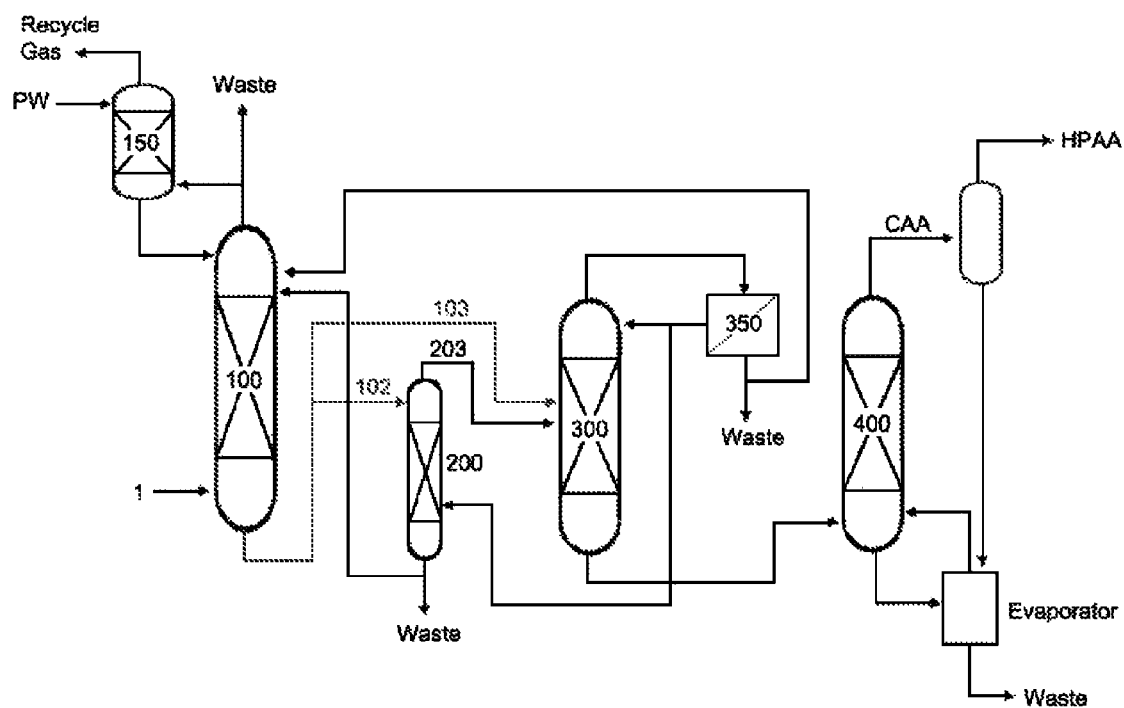

PROCESS FOR CONTINUOUS RECOVERING (METH)ACRYLIC ACID AND APPARATUS FOR THE PROCESS

This application is a Nation Phase Application of International Application No. PCT/KR2013/006101, filed on Jul. 9, 2013, which claims the benefit of Korean Application Nos. 10-2013-0080189 and 10-2012-0085339 filed on Jul. 9, 2013 and Aug. 3, 2012, respectively, all of which are hereby incorporated by reference in their entirety for all purposes as if fully set forth herein.

TECHNICAL FIELD

The present invention relates to a method of continuous recovery of (meth)acrylic acid and an apparatus used for the continuous recovery method.

BACKGROUND OF ART (Meth)acrylic acid is generally prepared by gas phase oxidation of propane, propylene, (meth)acrolein, and the like in the presence of a catalyst. For example, propane, propylene, and the like are converted to (meth)acrylic acid through (meth)acrolein by gas phase oxidation in the presence of an appropriate catalyst in a reactor, and a reaction product mixed gas including (meth)acrylic acid, non-reacted propane or propylene, (meth)acrolein, inert gas, carbon dioxide, water vapor, and various organic by-products (acetic acid, high boiling point by-products, and the like) is obtained in the back end of the reactor.

The (meth)acrylic acid-containing mixed gas contacts an absorption solvent such as process water and the like in a (meth)acrylic acid absorption tower, and is recovered as a (meth)acrylic acid aqueous solution. Further, (meth)acrylic acid-stripped insoluble gas is recycled for a synthesis reaction of (meth)acrylic acid, and a part thereof is incinerated, converted into harmless gas, and discharged. The (meth) acrylic acid aqueous solution is distilled and purified while passing through a water separation tower and the like, to obtain (meth)acrylic acid.

Meanwhile, in order to improve the recovery efficiency of (meth)acrylic acid, various methods of controlling process conditions or process sequence and the like have been suggested. Among them, as a method for separating water and acetic acid from the (meth)acrylic acid aqueous solution obtained in the (meth)acrylic acid absorption tower, an azeotropic distillation method is known, wherein acetic acid, the main by-product of a (meth)acrylic acid process, is recovered from the upper part of the water separation tower together with water using a hydrophobic azeotropic solvent in the water separation tower, and (meth)acrylic acid is recovered from the lower part of the water separation tower.

Particularly, the inventors suggested a method of recycling acetic acid-containing waste water that is recovered from the upper part of the water separation tower to the (meth)acrylic acid absorption tower and reusing it, in Korean Laid-Open Patent No. 2009-0041355.

The method of distilling a (meth)acrylic acid aqueous solution using a hydrophobic azeotropic solvent in the water separation tower may reduce the amount of waste water and simultaneously effectively prevent introduction of organic substances, and simplify a subsequent purification step.

However, the above method and previously disclosed recovery methods of (meth)acrylic acid have problems in that a very large amount of energy is consumed in the process of distilling a (meth)acrylic acid aqueous solution, and normal operation cannot be conducted due to the production of polymers by polymerization of (meth)acrylic acid, and thus operation stability is lowered.

DETAILED DESCRIPTION OF THE INVENTION

Technical Problem

It is an object of the invention to provide a method of continuous recovery of (meth)acrylic acid that may largely reduce energy consumption and yet exhibit improved operation stability.

It is another object of the invention to provide an apparatus for continuous recovery of (meth)acrylic acid.

Technical Solution

According to one embodiment of the invention, a method of continuous recovery of (meth)acrylic acid is provided, including:

contacting a mixed gas including (meth)acrylic acid, organic by-products, and vapor, which is produced by a synthesis reaction of (meth)acrylic acid, with water in a (meth)acrylic acid absorption tower (100) to obtain a (meth) acrylic acid aqueous solution;

dividing and feeding the (meth)acrylic acid aqueous solution to a (meth)acrylic acid extraction tower (200) and a water separation tower (300);

obtaining a (meth)acrylic acid extract with reduced water content from the (meth)acrylic acid aqueous solution that is fed to the (meth)acrylic acid extraction tower (200), and feeding it to a water separation tower (300); and distilling the (meth)acrylic acid aqueous solution and the (meth)acrylic acid extract that are fed to the water separation tower (300) to obtain (meth)acrylic acid.

The step of dividing and feeding the (meth)acrylic acid aqueous solution to a (meth)acrylic acid extraction tower (200) and a water separation tower (300) may be conducted in such a way that 5-70 wt % of the obtained (meth)acrylic acid aqueous solution is fed to the (meth)acrylic acid extraction tower (200), and the remainder is fed to the water separation tower (300).

The synthesis reaction of (meth)acrylic acid may be conducted by an oxidation reaction of at least one compound selected from the group consisting of propane, propylene, butane, isobutylene, t-butylene, and (meth)acrolein in the presence of a gas phase catalyst.

Meanwhile, the internal temperature of the (meth)acrylic acid absorption tower (100) may be maintained at 50 to 100° C.

The step of obtaining the (meth)acrylic acid aqueous solution may be conducted in such a way that a (meth) acrylic acid-containing aqueous solution is discharged to the lower part of the (meth)acrylic acid absorption tower (100), and (meth)acrylic acid-stripped non-condensable gas is discharged to the upper part of the (meth)acrylic acid absorption tower (100). In this case, the method for continuous recovery of (meth)acrylic acid according to the present invention may further include contacting the non-condensable gas with water to recover acetic acid that is included in the non-condensable gas.

In the water fed to the (meth)acrylic acid absorption tower (100), organic by-products may be included at a concentration of 3 to 20 wt %.

In the (meth)acrylic acid aqueous solution obtained in the (meth)acrylic acid absorption tower (100), (meth)acrylic acid may be included at a concentration of 40 to 90 wt %.

The (meth)acrylic acid extract may be obtained by contacting the (meth)acrylic acid aqueous solution that is fed to the (meth)acrylic acid extraction tower (200) with a hydrophobic extraction solvent to remove water included in the aqueous solution.

The (meth)acrylic acid extract may be obtained from the upper part of the (meth)acrylic acid extraction tower (200) and fed to the water separation tower (300), and at least a part of the lower discharged liquid of the (meth)acrylic acid extraction tower (200) may be fed to the upper end of the (meth)acrylic acid absorption tower (100) and used as an absorption solvent of (meth)acrylic acid. In the lower discharged liquid of the (meth)acrylic acid extraction tower (200), (meth)acrylic acid may be included at a concentration of 5 wt % or less. The upper end of the (meth)acrylic acid absorption tower (100) to which at least a part of the lower discharged liquid of the (meth)acrylic acid absorption tower (200) is fed may be at least one point corresponding to a height of 70% or more from the lowest part of the absorption tower.

The distillation in the water separation tower (300) may be conducted in the presence of a hydrophobic azeotropic solvent. Herein, the hydrophobic azeotropic solvent may include the same compound as the hydrophobic extraction solvent in the (meth)acrylic acid extraction tower (200).

By distillation in the water separation tower (300), discharged liquid including (meth)acrylic acid may be recovered from the lower part of the water separation tower (300), and discharged liquid including a hydrophobic azeotropic solvent, water, and acetic acid may be recovered from the upper part of the water separation tower (300).

At this time, the upper discharged liquid of the water separation tower (300) may be separated into an organic layer including the hydrophobic azeotropic solvent and an aqueous layer including acetic acid, at least a part of the organic layer may be fed to the upper end of the water separation tower (300) as an azeotropic solvent, and at least a part of the aqueous layer may be fed to the upper end of the (meth)acrylic acid absorption tower (100) as an absorption solvent.

According to another embodiment of the invention, an apparatus for continuous recovery of (meth)acrylic acid is provided, including:

a (meth)acrylic acid absorption tower (100) for contacting a mixed gas including organic by-products, vapor, and (meth)acrylic acid, which is produced by a synthesis reaction of (meth)acrylic acid, with water, to obtain a (meth) acrylic acid aqueous solution;

(meth)acrylic acid aqueous solution transfer lines (102 and 103) that are respectively connected from the (meth) acrylic acid absorption tower (100) to a (meth)acrylic acid extraction tower (200) and a water separation tower (300), to which the (meth)acrylic acid aqueous solution is divided and fed;

a (meth)acrylic acid extraction tower (200) for obtaining (meth)acrylic acid extract with reduced water content from the (meth)acrylic acid aqueous solution that is fed through the (meth)acrylic acid aqueous solution transfer line (102), and feeding it to a water separation tower (300);

a (meth)acrylic acid extract transfer line (203) that is connected from the (meth)acrylic acid extraction tower (200) to a water separation tower (300), to which the (meth)acrylic acid extract is fed; and a water separation tower (300) for distilling a (meth) acrylic acid aqueous solution fed through the (meth)acrylic acid aqueous solution transfer line (103), and (meth)acrylic acid extract fed through the (meth)acrylic acid extract transfer line (203), to obtain (meth)acrylic acid.

Advantageous Effects

The continuous recovery method of (meth)acrylic acid according to the present invention may maintain a recovery rate of (meth)acrylic acid equivalent to that of the previous recovery method, and yet may significantly reduce energy consumption, and may minimize polymerization of (meth) acrylic acid in the recovery process, thus providing more improved operation stability.

Specifically, the continuous recovery method of (meth) acrylic acid according to the present invention introduces a (meth)acrylic acid extraction tower (200) before a water separation tower (300) for distilling a (meth)acrylic acid aqueous solution to recover (meth)acrylic acid, thereby largely reducing an energy consumption amount in the water separation tower (300), thus improving energy efficiency of the total process.

Furthermore, the method according to the present invention divides and feeds the (meth)acrylic acid aqueous solution obtained from the (meth)acrylic acid absorption tower (100) to the (meth)acrylic acid extraction tower (200) and the water separation tower (300), thereby reducing the capacities of the (meth)acrylic acid extraction tower and the water separation tower, thus lowering facility load, and simultaneously maintaining treatment capacity of the (meth) acrylic acid aqueous solution fed from the (meth)acrylic acid absorption tower equivalent to that of the previous method, thus exhibiting high energy efficiency and improved productivity.

Further, since the method of the present invention may effectively divide treatment of the (meth)acrylic acid aqueous solution in the (meth)acrylic acid extraction tower (200) and the water separation tower (300), a load in the water separation tower (300) may be reduced, and thus temperature near the feed inlet of the water separation tower (300) may be maintained low, thus minimizing polymerization of (meth)acrylic acid during distillation to provide more improved operation stability.

BRIEF DESCRIPTION OF THE DRAWING

FIG. 1 is a flowchart schematically showing the continuous recovery method of (meth)acrylic acid according to one embodiment of the invention.

DETAILED DESCRIPTION OF THE EMBODIMENTS

Hereinafter, the method of continuous recovery of (meth) acrylic acid and the recovery apparatus according to specific embodiments of the invention will be explained.

Unless otherwise described, terms used herein are defined as follows.

First, '(meth)acrylic acid' generally refers to acrylic acid and/or methacrylic acid.

Second, '(meth)acrylic acid-containing mixed gas' generally refers to a mixed gas that may be produced when (meth)acrylic acid is prepared by gas phase oxidation. That is, according to one embodiment of the invention, the (meth)acrylic acid-containing mixed gas may be obtained by gas phase oxidation of at least one compound selected from the group consisting of propane, propylene, butane, i-butylene, t-butylene, and (meth)acrolein Craw material compound') in the presence of a catalyst, wherein the (meth) acrylic acid-containing mixed gas may include (meth) acrylic acid, non-reacted raw material compounds, (meth) acrolein, inert gas, carbon monoxide, carbon dioxide, water vapor, and various organic by-products (acetic acid, high boiling point by-products, and the like), and the like.

As used herein, low boiling point by-products' (light ends) or 'high boiling point by-products' (heavies) are kinds of by-products that can be produced in the process of preparation and recovery of (meth)acrylic acid, and generally refer to compounds having smaller or larger molecular weight than (meth)acrylic acid.

The term '(meth)acrylic acid aqueous solution' refers to an aqueous solution in which (meth)acrylic acid is dissolved, and for example, the (meth)acrylic acid aqueous solution may be obtained by contacting the (meth)acrylic acid-containing mixed gas with water.

The term '(meth)acrylic acid extract' refers to an aqueous solution having a relatively higher concentration of (meth) acrylic acid than the (meth)acrylic acid aqueous solution, and for example, the meth)acrylic acid extract may be obtained by lowering the content of water included in the (meth)acrylic acid aqueous solution in a (meth)acrylic acid extraction tower (200).

Meanwhile, the technical terms used herein are only to mention specific embodiments, and are not intended to limit the invention.

Singular forms used herein include plural forms, unless they have clearly opposite meanings.

The meaning of 'comprising' as used herein embodies specific property, area, integer, step, operation, element, or component, and it does not exclude the addition of other specific properties, areas, integers, steps, operations, elements, or components.

Hereinafter, referring to the attached drawings, specific embodiments of the invention will be explained in detail so that one of ordinary knowledge in the art may easily practice it. However, the present invention may be embodied in various forms, and is not limited to the examples.

The inventors confirmed during studies on the continuous recovery method of (meth)acrylic acid that the previously disclosed recovery method of (meth)acrylic acid through azeotropic distillation has problems in that a very large amount of energy is consumed in a water separation tower (or distillation tower) for distilling a (meth)acrylic acid aqueous solution, and operation stability is lowered due to the production of a polymer by polymerization of (meth) acrylic acid.

Therefore, the inventors confirmed during repeated studies for improving these problems that if a (meth)acrylic acid extraction tower (200) is introduced before a water separation tower (300) for distilling a (meth)acrylic acid aqueous solution that is obtained in a (meth)acrylic acid absorption tower (100), and particularly, if the (meth)acrylic acid aqueous solution obtained in the (meth)acrylic acid absorption tower (100) is divided and fed to the (meth)acrylic acid extraction tower (200) and the water separation tower (300), as shown in FIG. 1, energy efficiency of the total process may be improved. Furthermore, the inventors confirmed that the process of FIG. 1 may effectively divide the load of the water separation tower (300), thus minimizing a polymerization reaction of (meth)acrylic acid in a distillation process, to provide more improved operation stability.

Thus, according to one embodiment of the invention, a method of continuous recovery of (meth)acrylic acid is provided, including:

contacting a mixed gas including (meth)acrylic acid, organic by-products, and vapor, which is produced by a synthesis reaction of (meth)acrylic acid, with water in a (meth)acrylic acid absorption tower (100) to obtain a (meth) acrylic acid aqueous solution;

dividing and feeding the (meth)acrylic acid aqueous solution to a (meth)acrylic acid extraction tower (200) and a water separation tower (300);

obtaining a (meth)acrylic acid extract with reduced water content from the (meth)acrylic acid aqueous solution that is fed to the (meth)acrylic acid extraction tower (200), and feeding it to a water separation tower (300); and distilling the (meth)acrylic acid aqueous solution and the (meth)acrylic acid extract that are fed to the water separation tower (300) to obtain (meth)acrylic acid.

Hereinafter, referring to FIG. 1, each step of the continuous recovery method of (meth)acrylic acid according to the present invention will be explained.

First, the method of continuous recovery of (meth)acrylic acid according to the present invention includes a step of obtaining a (meth)acrylic acid aqueous solution.

Since the (meth)acrylic acid aqueous solution may be obtained by a common method in the technical field to which the invention pertains, the method is not specifically limited. However, according to the present invention, this step may be conducted by contacting a mixed gas including (meth) acrylic acid, organic by-products, and vapor, which is produced by a synthesis reaction of (meth)acrylic acid, with an absorption solvent in a (meth)acrylic acid absorption tower (100) to obtain a (meth)acrylic acid aqueous solution.

Herein, the synthesis reaction of the (meth)acrylic acid may be conducted by an oxidation reaction of at least one compound selected from the group consisting of propane, propylene, butane, isobutylene, t-butylene, and (meth)acrolein in the presence of a gas phase catalyst.

The gas phase oxidation reaction may be progressed in a gas phase oxidation reactor of a common structure and under common reaction conditions. As the catalyst of the gas phase oxidation reaction, common catalysts may be used, and preferably, catalysts described in Korean Registered Patent No. 0349602 and No. 037818, and the like may be used. However, the gas phase oxidation reaction is not limited to the above examples in the present invention.

In the (meth)acrylic acid-containing mixed gas produced by the gas phase oxidation reaction, unreacted raw material compounds, intermediate (meth)acrolein, other inert gasses, carbon dioxide, vapor, and various organic by-products (acetic acid, low boiling point by-products, high boiling point by-products, and the like), and the like may be included, in addition to the end product (meth)acrylic acid.

According to the present invention, the (meth)acrylic acid-containing mixed gas (1) may be fed to the (meth) acrylic acid absorption tower (100) and contact with absorption solvent water, and thereby be obtained in the form of an aqueous solution in which (meth)acrylic acid is dissolved.

The (meth)acrylic acid absorption tower (100) may be in the form of a packed column including fillers such as raschig rings, pall rings, a saddles, gauze, a structured packing, and the like, or a common multistage column, so as to improve contact efficiency of the (meth)acrylic acid-containing mixed gas (1) with an absorption solvent.

According to the present invention, the (meth)acrylic acid-containing mixed gas (1) may be fed to the lower part of the (meth)acrylic acid absorption tower (100), and an absorption solvent for absorbing (meth)acrylic acid included in the mixed gas (1) is fed to the upper part of the (meth)acrylic acid absorption tower (100).

The absorption solvent of the (meth)acrylic acid may be water such as tap water, deionized water, and the like, and the absorption solvent may include cycle process water that is introduced from a different process. Thus, the absorption solvent may include a trace amount of organic by-products (for example, acetic acid) introduced from a different process, and according to one embodiment of the invention, in the absorption solvent fed to the (meth)acrylic acid absorption tower (100), organic by-products may be included at a concentration of 3 to 20 wt %.

That is, considering absorption efficiency of (meth)acrylic acid in the (meth)acrylic acid absorption tower (100), it is preferable that the absorption solvent (particularly, cycle process water) fed to the (meth)acrylic acid absorption tower (100) includes 20 wt % or less of organic by-products.

Meanwhile, the (meth)acrylic acid absorption tower (100) may be operated at the internal pressure of 1 to 1.5 bar, preferably 1 to 1.3 bar, considering the condensation condition of (meth)acrylic acid and moisture content condition according to saturated water vapor pressure, and the like; and the internal temperature of the (meth)acrylic acid absorption tower (100) may be controlled to 50 to 100° C., preferably 50 to 80° C.

Through the above process, a (meth)acrylic acid aqueous solution is discharged to the lower part of the (meth)acrylic acid absorption tower (100), and (meth)acrylic acid-stripped non-condensable gas may be discharged to the upper part of the (meth)acrylic acid absorption tower (100).

Herein, it is advantageous in terms of improvement in process efficiency that the (meth)acrylic acid aqueous solution that is discharged to the lower part of the (meth)acrylic acid absorption tower (100) includes (meth)acrylic acid at a concentration of 40 to 90 wt %, preferably 50 to 90 wt %, and more preferably 50 to 80 wt %.

Meanwhile, at least a part of the non-condensable gas that is discharged to the upper part of the (meth)acrylic acid absorption tower (100) may be fed to a step of recovering organic by-products (particularly acetic acid) included in the non-condensable gas, and the remainder may be fed to a waste gas incinerator. That is, according to one embodiment of the invention, a step of contacting non-condensable gas that is discharged to the upper part of the (meth)acrylic acid absorption tower (100) with absorption solvent water to recover acetic acid included in the non-condensable gas may be further conducted.

According to the present invention, the step of contacting non-condensable gas with an absorption solvent may be conducted in an acetic acid absorption tower (150). Further, for an effective acetic acid absorption process, the acetic acid absorption tower (150) may be operated at a pressure of 1 to 1.5 bar, and preferably 1 to 1.3 bar, and the internal temperature of the acetic acid absorption tower (150) may be controlled to 50 to 100° C., and preferably 50 to 80° C. Further, specific operation conditions of the acetic acid absorption tower (150) may follow Korean Laid-Open Patent No. 2009-0041355 of the applicant.

Herein, an absorption solvent for absorbing particularly acetic acid among the organic by-products included in the non-condensable gas may be fed to the upper part of the acetic acid absorption tower (150), and an aqueous solution containing acetic acid may be discharged to the lower part of the acetic acid absorption tower (150).

As the acetic acid absorption solvent, the same kind as the above-explained (meth)acrylic acid absorption solvent may be used, and preferably, the acetic acid-containing aqueous solution that is discharged from the acetic acid absorption tower (150) may be fed to the (meth)acrylic acid absorption tower (100) and used as an absorption solvent. Further, acetic acid-stripped gas is discharged to the upper part of the acetic acid absorption tower (150), and may be recycled to the above-explained (meth)acrylic acid synthesis reaction step and reused.

Meanwhile, the method of continuous recovery of (meth)acrylic acid includes a step of dividing and feeding the (meth)acrylic acid aqueous solution that is discharged from the (meth)acrylic acid absorption tower (100) to the (meth)acrylic acid extraction tower (200) the a water separation tower (300).

According to the present invention, as shown in FIG. 1, the (meth)acrylic acid absorption tower (100) is connected simultaneously to the (meth)acrylic acid extraction tower (200) and the water separation tower (300) through (meth)acrylic acid aqueous solution transfer lines (102 and 103), respectively, and the (meth)acrylic acid extraction tower (200) is connected to the water separation tower (300) through a (meth)acrylic acid extract transfer line (203).

The (meth)acrylic acid extraction tower (200) is an apparatus for removing water that has been used as an absorption solvent in the step of obtaining a (meth)acrylic acid aqueous solution and recovering an extract with a higher concentration of (meth)acrylic acid therefrom.

Further, the water separation tower (300) is an apparatus for azeotropically distilling the (meth)acrylic acid aqueous solution fed from the (meth)acrylic acid absorption tower (100) and the (meth)acrylic acid extract fed from the (meth)acrylic acid extraction tower (200), to recover (meth)acrylic acid therefrom. The (meth)acrylic acid extraction tower (200) and the water separation tower (300) will be explained later.

As explained above, in the previously disclosed recovery method of (meth)acrylic acid through azeotropic distillation, the whole (meth)acrylic acid aqueous solution obtained from the (meth)acrylic acid absorption tower (100) is fed to a water separation tower (300) and distilled.

To the contrary, the method of continuous recovery of (meth)acrylic acid according to the present invention introduces a (meth)acrylic acid extraction tower (200) before the water separation tower (300), thereby largely reducing treatment load of the (meth)acrylic acid aqueous solution in the water separation tower (300) and energy consumption amount.

Furthermore, the method of the present invention divides and supplies the (meth)acrylic acid aqueous solution obtained from the (meth)acrylic acid absorption tower (100) to the (meth)acrylic acid extraction tower (200) and the water separation tower (300), thereby reducing total facility load, and simultaneously minimizing a polymerization reaction of (meth)acrylic acid in the water separation tower (300), thus providing more improved operation stability.

According to the present invention, the ratio of dividing and feeding the (meth)acrylic acid obtained from the (meth)acrylic acid absorption tower (100) to the (meth)acrylic acid extraction tower (200) and the water separation tower (300) may be determined considering a capacity ratio of the (meth)acrylic acid extraction tower (200) and the water separation tower (300), treatment capacity, energy efficiency improvement effect of the total process, and the like.

Taking the above conditions into consideration, it is advantageous for 5~70 wt %, more preferably 20~50 wt %, of the (meth)acrylic acid aqueous solution obtained from the (meth)acrylic acid absorption tower (100) to be fed to the (meth)acrylic acid extraction tower (200), and the remainder may be fed to the water separation tower (300).

In other words, the content ratio (wt %) of the (meth)acrylic acid aqueous solution divided and fed from the (meth)acrylic acid absorption tower (100) to the (meth)acrylic acid extraction tower (200) and the water separation tower (300) may be 5:95, 10:90, 15:85, 20:80, 25:75, 30:70, 35:65, 40:60, 45:55, 50:50, 55:45, 60:40, 65:35, 70:30, or the like, preferably 20:80 to 70:30, more preferably 30:70 to 60:40, and most preferably 40:60 to 50:50. However, the present invention is not limited to the above exemplified ratios, and the ratio may be variously controlled within the above range, considering the purpose and the effect of the present invention.

According to the present invention, as the amount of the (meth)acrylic acid aqueous solution fed to the (meth)acrylic acid extraction tower (200) becomes larger, the effect of dividing treatment with the water separation tower (300) may be improved, and thus energy efficiency of the total process may be improved.

However, if excessive (meth)acrylic acid aqueous solution is fed to the extraction tower (200), an extraction tower (200) having larger capacity may be required, the operation conditions of the water separation tower (300) at the back end may become inferior, thus increasing loss of (meth)acrylic acid to lower process efficiency, and thus it is advantageous for the feed ratio of the (meth)acrylic acid aqueous solution to be controlled within the above-explained range.

Further, as the amount of the (meth)acrylic acid aqueous solution fed to the water separation tower (300) becomes larger, the amount of water that should be removed by azeotropic distillation in the water separation tower (300) may be increased, thus lowering the effect of reducing energy consumption, such that it is advantageous for the feed ratio of the (meth)acrylic acid aqueous solution to be controlled within the above-explained range.

The (meth)acrylic acid aqueous solution may be divided and fed from the (meth)acrylic acid absorption tower (100) through the (meth)acrylic acid aqueous solution transfer lines (102 and 103) respectively connected to the (meth)acrylic acid extraction tower (200) and the water separation tower (300). The (meth)acrylic acid aqueous solution may be divided and fed at the above-explained ratio by common means installed in the transfer lines (102 and 103).

Meanwhile, the method of continuous recovery of (meth)acrylic acid according to the present invention includes a step of obtaining a (meth)acrylic acid extract with reduced water content from the (meth)acrylic acid aqueous solution that is fed to the (meth)acrylic acid extraction tower (200), and feeding it to the water separation tower (300) (hereinafter referred to as an 'extraction process').

According to the present invention, the (meth)acrylic acid extraction tower (200) receives a part of the (meth)acrylic acid aqueous solution obtained from the (meth)acrylic acid absorption tower (100), removes most of water included in the (meth)acrylic acid aqueous solution without using a significant amount of energy, and feeds it to the water separation tower (300), thereby reducing energy used for azeotropic distillation in the water separation tower (300) as described below.

Herein, the (meth)acrylic acid extract may be obtained by contacting the (meth)acrylic acid aqueous solution that is fed to the (meth)acrylic acid extraction tower (200) with a hydrophobic extraction solvent to remove water included in the aqueous solution. That is, it is preferable in terms of improvement in energy efficiency of the total process for the extraction in the (meth)acrylic acid extraction tower (200) to use a liquid-liquid contact method.

The hydrophobic extraction solvent may be a hydrocarbon solvent that forms an azeotrope with water and organic by-products (acetic acid and the like), and that does not form an azeotrope with (meth)acrylic acid but can sufficiently extract it. Further, it may have a boiling point of 10 to 120° C. so as to improve extraction process efficiency.

According to the present invention, the hydrophobic extraction solvent satisfying the above properties may be at least one solvent selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

Meanwhile, it is advantageous in terms of improvement in process efficiency for the temperature of the (meth)acrylic acid aqueous solution to be 10 to 70° C. in the extraction process, and for the weight ratio of the hydrophobic extraction solvent to the (meth)acrylic acid aqueous solution to be 1:1 to 1:5, preferably 1:1.2 to 1:2.5.

Further, for the extraction process, a common extraction apparatus according to a liquid-liquid contact method may be used. Non-limiting examples of the extraction apparatus may include a Karr reciprocating plate column, a rotary-disk contactor, a Scheibel column, a Kuhni column, a spray extraction tower, a packed extraction tower, a pulsed packed column, a mixer-settler, a centrifugal counter current extractor, and the like.

By this method, (meth)acrylic acid extract from which most water included in the (meth)acrylic acid aqueous solution has been removed may be obtained, and preferably, (meth)acrylic acid extract is discharged to the upper part of the (meth)acrylic acid extraction tower (200), and the discharged extract is fed to the water separation tower (300) through the (meth)acrylic acid extract transfer line (203).

In addition, at least a part of the lower discharged liquid of the (meth)acrylic acid extraction tower (200) may be fed to the upper end of the (meth)acrylic acid absorption tower (100) and used as a part of the (meth)acrylic acid absorption solvent, and a part of the lower discharged liquid may be treated as waste water.

It is also preferable in terms of improvement in the efficiency of the absorption process for the upper end of the (meth)acrylic acid absorption tower (100) to which the lower discharged liquid of the extraction tower (200) is recycled to be at least one point corresponding to the height of 70% or more from the lowest part of the absorption tower (100). In addition, it is preferable that (meth)acrylic acid is not included in the lower discharged liquid of the (meth)acrylic acid extraction tower (200), but it may be included a little, and the amount may be preferably 5 wt % or less.

Meanwhile, the method of continuous recovery of (meth)acrylic acid according to the present invention includes a step of distilling the (meth)acrylic acid aqueous solution and the (meth)acrylic acid extract that are fed to the water separation tower (300) to obtain (meth)acrylic acid (hereinafter referred to as a 'distillation process').

The distillation process is a process for azeotropically distilling the (meth)acrylic acid aqueous solution that is fed from the (meth)acrylic acid absorption tower (100) to the water separation tower (300) and the (meth)acrylic acid extract that is fed from the (meth)acrylic acid extraction tower (200) to the water separation tower (300), thereby removing water and organic by-products and separating and obtaining (meth)acrylic acid.

The (meth)acrylic acid aqueous solution and the (meth)acrylic acid extract are fed to the water separation tower (300) respectively through separate transfer lines (103 and 203), wherein the location of the water separation tower (300) to which each solution is fed may be the same or different, but it is advantageous in terms of improvement in the process efficiency for the solutions to be fed to the same location.

Meanwhile, according to the present invention, it is advantageous for the distillation in the water separation tower (300) to be conducted in the presence of a hydrophobic azeotropic solvent, because it may simultaneously recover water and organic by-products (acetic acid and the like).

The hydrophobic azeotropic solvent is a hydrophobic solvent that can form an azeotrope with water and acetic acid, and that does not form an azeotrope with (meth)acrylic acid, and hydrocarbon solvents satisfying the above properties may be used without specific limitations. Further, the hydrophobic azeotropic solvent may have a lower boiling point than (meth)acrylic acid, and preferably, it may have a boiling point of 10 to 120° C.

The hydrophobic azeotropic solvents satisfying the above properties may include at least one selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

The hydrophobic azeotropic solvent may be identical to or different from the hydrophobic extraction solvent that is applied for the (meth)acrylic acid extraction tower (200). However, considering the production efficiency according to the continuous process, the hydrophobic azeotropic solvent preferably includes the same compounds as the hydrophobic extraction solvent.

As such, if the same compound is used as the azeotropic solvent and the extraction solvent, at least a part of the azeotropic solvent that is distilled in the water separation tower (300) and recovered may be fed to the lower part of the (meth)acrylic acid extraction tower (200) and used as a part of the extraction solvent.

Meanwhile, the water separation tower (300) may be equipped with a packed column or multistage column including the above-explained filler, preferably a sieve tray column or a dual flow tray column, therein.

If the hydrophobic azeotropic solvent is introduced into the upper part of the water separation tower (300), the azeotrope of (meth)acrylic acid and the absorption solvent (for example, water) may be broken. Thus, water and acetic acid in the (meth)acrylic acid aqueous solution directly fed from the (meth)acrylic acid absorption tower (100); a part of water, acetic acid, and hydrophobic extraction solvent that are not removed in the (meth)acrylic acid extraction tower (200); and the hydrophobic azeotropic solvent used for azeotropic distillation may form an azeotrope and be recovered from the upper part of the water separation tower (300). Further, discharged liquid containing (meth)acrylic acid may be recovered from the lower part of the water separation tower (300).

The upper discharged liquid of the water separation tower (300) may be fed to a phase separator (350) and subjected to predetermined treatment and then reused. The phase separator (350) is an apparatus for separating liquid phases that are not mixed with each other using gravity or centrifugal force, and the like, and a relatively light liquid may be recovered from the upper part of the phase separator (350), while a relatively heavy liquid may be recovered from the lower part of the phase separator (350).

In the present invention, for example, in case water is used as an absorption solvent of (meth)acrylic acid, the upper discharged liquid that is fed to the phase separator (350) may be separated into an organic layer containing a hydrophobic azeotropic solvent and an aqueous layer containing water.

At least a part of the organic layer that is separated in the phase separator (350) may be fed to the upper end of the water separation tower (300) and used as an azeotropic solvent, and the remainder of the organic layer may be fed to the (meth)acrylic acid extraction tower (200) and used as an extraction solvent, as necessary. At least a part of the aqueous layer that is separated in the phase separator (350) may be fed to the upper end of the (meth)acrylic acid absorption tower (100) and used as an absorption solvent, and a part thereof may be treated as waste water.

Acetic acid may be included in the water layer, and the concentration of acetic acid included in the aqueous layer may be varied according to the kind of azeotropic solvents and reflux ratio of the column installed in the water separation tower, and the like. According to the present invention, the concentration of acetic acid included in the aqueous layer of the upper discharged liquid may be 1 to 50 wt %, preferably 2 to 40 wt %, more preferably 3 to 30 wt %.

Meanwhile, discharged liquid containing (meth)acrylic acid is recovered from the lower part of the water separation tower (300), which is crude (meth)acetic acid, and may be fed to an additional purification process as necessary.

Water, acetic acid, and the azeotropic solvent may be included in the lower discharged liquid of the water separation tower (300), and preferably, the water, the acetic acid, and the azeotropic solvent may be included respectively in an amount of less than 0.1 wt %, so that the lower discharged liquid may be used as crude (meth)acrylic acid.

While the (meth)acrylic acid aqueous solution passes through the (meth)acrylic acid absorption tower (100), the (meth)acrylic acid extraction tower (200), the water separation tower (300), and the like, at least a part of (meth)acrylic acid included in the aqueous solution may be polymerized to produce a polymer such as a dimer or oligomer and the like. In order to minimize the polymerization of (meth)acrylic acid, a polymerization inhibitor may be added to the water separation tower (300), and commonly used polymerization inhibitors may be used without specific limitations.

Meanwhile, in the lower discharged liquid of the water separation tower (300), high boiling point by-products such as a (meth)acrylic acid polymer, a polymerization inhibitor, and the like may be included in addition to (meth)acrylic acid. Thus, as necessary, a step of feeding the lower discharged liquid of the water separation tower (300) to a high boiling point by-product separation tower (400) to separate high boiling point by-products included in the lower discharged liquid may be further conducted.

The high boiling point by-product separation tower (400) may have a common structure, it may be operated under common reaction conditions, and the construction and reaction conditions of the separation tower are not specifically limited. High boiling point by-products included in the lower discharged liquid of the water separation tower (300)

may be recovered from the lower part of the high boiling point by-product separation tower (400), and crude (meth) acrylic acid (CAA) free of high boiling point by-products may be recovered from the upper part of the high boiling point by-product separation tower (400).

The crude (meth)acrylic acid (CAA) may be obtained as high purity (meth)acrylic acid (HPAA) through an additional crystallization process.

Each step that can be included in the method of recovery of (meth)acrylic acid according to the present invention may be conducted continuously, and besides the above-explained steps, any steps commonly conducted in the technical field to which the invention pertains may be further conducted before or after each step.

For example, a process of feeding the (meth)acrylic acid aqueous solution obtained in the (meth)acrylic acid absorption tower (100) to a separate stripping tower, before dividing and feeding it to the (meth)acrylic acid extraction tower (200) and the water separation tower (300) so as to remove low boiling point by-products (acrolein, propionaldehyde, acetaldehyde, formaldehyde, isopropyl acetate, and the like) dissolved in the (meth)acrylic acid aqueous solution may be further conducted.

Meanwhile, according to another embodiment of the invention, an apparatus for continuous recovery of (meth) acrylic acid is provided, including:

a (meth)acrylic acid absorption tower (100) for contacting mixed gas including organic by-products, vapor, and (meth) acrylic acid, which is produced by a synthesis reaction of (meth)acrylic acid, with water, to obtain a (meth)acrylic acid aqueous solution;

(meth)acrylic acid aqueous solution transfer lines (102 and 103) that are connected from the (meth)acrylic acid absorption tower (100) to the (meth)acrylic acid extraction tower (200) and the water separation tower (300) respectively, to which the (meth)acrylic acid aqueous solution is divided and fed;

a (meth)acrylic acid extraction tower (200) for obtaining (meth)acrylic acid extract with reduced water content from the (meth)acrylic acid aqueous solution that is fed through the (meth)acrylic acid aqueous solution transfer line (102), and feeding it to a water separation tower (300);

a (meth)acrylic acid extract transfer line (203) that is connected from the (meth)acrylic acid extraction tower (200) to the water separation tower (300), to which the (meth)acrylic acid extract is fed; and the water separation tower (300) for distilling the (meth) acrylic acid aqueous solution fed through the (meth)acrylic acid aqueous solution transfer line (103) and the (meth) acrylic acid extract fed through the (meth)acrylic acid extract transfer line (203) to obtain (meth)acrylic acid.

Specifically, in the apparatus according to the present invention, the (meth)acrylic acid absorption tower (100) is connected simultaneously to the (meth)acrylic acid extraction tower (200) and the water separation tower (300) through each (meth)acrylic acid aqueous solution transfer line (102 and 103), and the (meth)acrylic acid extraction tower (200) is connected to the water separation tower (300) through a (meth)acrylic acid extract transfer line (203).

According to the present invention, the (meth)acrylic acid absorption tower (100) may be in the form of a packed column or a multistage column including fillers such as raschig rings, pall rings, a saddles, a gauze, a structure packing, and the like therein, so as to improve contact efficiency of the (meth)acrylic acid-containing mixed gas (1) with an absorption solvent water.

As the (meth)acrylic acid extraction tower (200), a common extractor according to a liquid-liquid contact method may be used, and non-limiting examples thereof may include a Karr reciprocating plate column, a rotary-disk contactor, a Scheibel column, a Kuhni column, a spray extraction tower, a packed extraction tower, a pulsed packed column, a mixer-settler, a centrifugal counter current extractor, and the like.

The water separation tower (300) may be equipped with a pack column or a multistage column including the above-explained fillers, preferably a sieve tray column or a dual flow tray column, therein.

In addition, the acetic acid absorption tower (150), the (meth)acrylic acid aqueous solution transfer lines (102 and 103), the (meth)acrylic acid extract transfer line (203), the phase separator (350), the high boiling point by-product separation tower (400), and the like, which are shown in FIG. 1, may have constructions common in the technical field to which the invention pertains, and the action and effect in each process are as explained above.

Hereinafter, preferable examples are presented to aid in understanding of the invention. However, these examples are only to illustrate the invention, and the invention is not limited thereto.

EXAMPLE 1

In order to verify the effects of energy reduction and improvement in operation stability of the water separation tower (300) resulting from the dividing and feeding of the (meth)acrylic acid aqueous solution obtained in the (meth) acrylic acid absorption tower (100) to the (meth)acrylic acid extraction tower (200) and the water separation tower (300), a continuous recovery apparatus having the construction as shown in FIG. 1 was prepared, and the following process was continuously conducted.

I. (Meth)Acrylic Acid Absorption Tower—Preparation of an Acrylic Acid Aqueous Solution The reaction gas obtained by oxidation of propylene was introduced into a (meth)acrylic acid absorption tower (100) to obtain an acrylic acid aqueous solution (composition: about 68 wt % of acrylic acid, about 2 wt % of acetic acid, and about 30 wt % of water) from the lower part of the (meth)acrylic acid absorption tower (100) using water as a (meth)acrylic acid absorption solvent.

The acrylic acid aqueous solution was divided and fed to a (meth)acrylic acid extraction tower (200) and a water separation tower (300) at the weight ratio of 35:65.

II. (Meth)Acrylic Acid Extraction Tower—Removal of Water from the Acrylic Acid Aqueous Solution As a (meth)acrylic acid extraction tower (200), a Karr type liquid-liquid reciprocating extractor having an inner diameter of 22 mm and a total of 56 stages was used. 35 wt % of the acrylic acid aqueous solution discharged to the lower part of the (meth)acrylic acid absorption tower was introduced through a first stage, the uppermost stage of the extraction tower (200), at a flow rate of about 91.09 g/min. A part of reflux flow containing toluene obtained as an organic layer in the upper discharged liquid of the water separation tower (300) described below was used as an extraction solvent, and the extraction solvent was introduced through a $56^{th}$ stage, the lowest stage of the extraction tower (200), at a flow rate of about 118.73 g/min.

After stable operation was conducted, at a steady state, an acrylic acid extract (composition: about 64.8 wt % of toluene, about 32.9 wt % of acrylic acid, about 1.6 wt % of water, and about 0.6 wt % of acetic acid) was obtained from the upper part of the extraction tower (200), and water (composition: about 95.1 wt % of water, about 1.8 wt % of acrylic acid, and about 3.1 wt % of acetic acid) was discharged to the lower part of the extraction tower (200). As the result of operation of the (meth)acrylic acid extraction tower (200), the removal rate of water from the acrylic acid aqueous solution fed from the (meth)acrylic acid absorption tower (100) was measured to be about 89.7%, and the removal rate of acetic acid was measured to be about 65.6%. Further, the acrylic acid extract discharged to the upper part of the extraction tower (200) was fed to the water separation tower (300).

III. Water Separation Tower—Azeotropic Distillation

As the water separation tower (300), a dual flow tray pilot column having an inner diameter of 30 mm and a total of 28 stages was used, and the operation pressure was maintained at 110 torr.

To the water separation tower (300), 65 wt % of the acrylic acid aqueous solution that is discharged to the lower part of the (meth)acrylic acid absorption tower (100) and the acrylic acid extract that is discharged to the upper part of the (meth)acrylic acid extraction tower (200) were fed. At this time, the acrylic acid aqueous solution was introduced into the 14$^{th}$ stage from the upper part of the water separation tower (300) at a flow rate of about 6.08 g/min, and the acrylic acid extract was introduced into the 14$^{th}$ stage from the upper part of the water separation tower (300) at a flow rate of about 6.55 g/min. A part of the toluene reflux flow that is separated from a phase separator (350) was introduced to the first stage, the uppermost stage of the water separation tower (300), at a flow rate of about 7.66 g/min as an azeotropic solvent.

Heat was fed through a reboiler at the lower stage of the water separation tower (300) so that the temperature of the 16$^{th}$ stage of the water separation tower (300) became about 86° C. or more, and the temperature of the 12nd stage may not exceed about 58° C. After stable operation was conducted for about 10 hours at a steady state, a distillate was discharged to the upper part of the water separation tower (300) at a flow rate of 14.01 g/min, and an acrylic acid flow of 6.29 g/min was obtained from the lower part of the water separation tower (300). Herein, at a steady state, the temperature of the upper part of the water separation tower (300) was maintained at about 40.1° C., and the temperature of the lower part was maintained at about 96.9° C.

As the result of the operation of the water separation tower (300), the removal rate of water and acetic acid included in the acrylic acid extract and the acrylic acid aqueous solution fed to the water separation tower was about 99% or more, acrylic acid flow wherein most water and acetic acid were removed could be obtained from the lower part of the water separation tower (300), and acrylic acid that was lost to the upper part of the water separation tower (300) was about 0.22 wt %.

The water separation tower (300) could be operated stably without producing a polymer in the tower even after 10 days of long term operation.

The following Table 1 shows the flow rate and the concentration of each flow at a steady state operation of the water separation tower (300).

TABLE 1

|  |  | Acrylic acid aqueous solution | Acrylic acid extract flow | Reflux flow of azeotropic solvent | Upper flow of water separation tower | Lower flow of water separation tower |
| --- | --- | --- | --- | --- | --- | --- |
| Mass Flow (g/min) |  | 6.08 | 6.55 | 7.66 | 14.01 | 6.29 |
| Composition (wt %) | Toluene | 0.00 | 64.88 | 99.74 | 84.58 | 0.00 |
|  | Acrylic acid | 67.99 | 32.90 | 0.10 | 0.22 | 99.95 |
|  | Acetic acid | 2.00 | 0.66 | 0.16 | 1.22 | 0.03 |
|  | Water | 29.22 | 1.55 | 0.00 | 13.98 | 0.00 |
|  | Heavies | 0.02 | 0.02 | 0.00 | 0.00 | 0.03 |

The treatment amount of the acrylic acid aqueous solution through the (meth)acrylic acid absorption tower (100), (meth)acrylic acid extraction tower (200), and water separation tower (300) was about 9.4 g per minute, the production amount of acrylic acid was about 6.3 g per minute, and total recovery rate of acrylic acid was about 99.6%. As a result of calculating energy consumption amount using an ASPEN PLUS process simulator program (AspenTech Inc.), it was confirmed that 22.7 cal was consumed per 1 g of the obtained acrylic acid.

EXAMPLE 2

An acrylic acid aqueous solution was obtained from the (meth)acrylic acid absorption tower (100) by the same method as Example 1.

The obtained acrylic acid aqueous solution was fed to the (meth)acrylic acid extraction tower (200) and the water separation tower (300) in the amount of each 50 wt %. Herein, the acrylic acid aqueous solution discharged from the (meth)acrylic acid absorption tower (100) and the acrylic acid extract discharged from the (meth)acrylic acid extraction tower (200) were introduced into the 14$^{th}$ stage from the upper part of the water separation tower (300), respectively at a flow rate of about 5.75 g/min and about 11.5 g/min.

The toluene reflux flow of the upper part of the water separation tower (300) was introduced into the first stage that is the uppermost stage at a flow rate of 4.4 g/min. Heat was fed through a reboiler at the lower part of the water separation tower (300) so that the temperature of the 16$^{th}$ stage became about 81° C. or more, and the temperature of the 12nd stage may not exceed about 49° C.

After stable operation was conducted for about 10 hours, at a steady state, distillate was discharged to the upper part of the water separation tower (300) at a flow rate of about 14.0 g/min, and acrylic acid flow of about 7.65 g/min was obtained from the lower part of the water separation tower (300). Herein, at a steady state, the temperature of the upper part of the water separation tower (300) was maintained at about 40.4° C., and the temperature of the lower part was maintained at about 96.2° C.

As a result of operation of the water separation tower (300), the removal rate of water and acetic acid included in the acrylic acid extract and the acrylic acid aqueous solution fed to the water separation tower was about 98% or more, acrylic acid flow wherein most water and acetic acid were removed could be obtained from the lower part of the water separation tower, and acrylic acid lost to the upper part of the water separation tower was about 0.50 wt %.

The water separation tower (300) could be operated stably without producing a polymer in the tower even after 10 days of long term operation.

The following Table 2 shows the flow rate and the concentration of each flow at steady stage operation of the water separation tower (300).

TABLE 2

|  |  | Acrylic acid aqueous solution | Acrylic acid extract flow | Reflux flow of azeotropic solvent | Upper flow of water separation tower | Lower flow of water separation tower |
|---|---|---|---|---|---|---|
| Mass Flow (g/min) |  | 5.75 | 11.50 | 4.40 | 14.00 | 7.65 |
| Composition (wt %) | Toluene | 0.00 | 64.88 | 99.74 | 84.07 | 0.00 |
|  | Acrylic acid | 67.99 | 32.90 | 0.10 | 0.50 | 99.92 |
|  | Acetic acid | 2.00 | 0.66 | 0.16 | 1.40 | 0.05 |
|  | Water | 29.99 | 1.55 | 0.00 | 14.03 | 0.00 |
|  | Heavies | 0.02 | 0.02 | 0.00 | 0.00 | 0.04 |

The treatment amount of the acrylic acid aqueous solution through the (meth)acrylic acid absorption tower (100), (meth)acrylic acid extraction tower (200), and water separation tower (300) was about 11.5 g per minute, the production amount of acrylic acid was about 7.65 g per minute, and total recovery rate of acrylic acid was about 99.1%. As a result of calculating energy consumption amount using an ASPEN PLUS process simulator program (AspenTech Inc.), it was confirmed that 18.7 cal was consumed per 1 g of the obtained acrylic acid.

Comparative Example 1

Azeotropic Distillation by Feeding the Total Amount of an Acrylic Acid Aqueous Solution to a Water Separation Tower An acrylic acid aqueous solution was obtained from the (meth)acrylic acid absorption tower (100) by the same method as Example 1.

The total amount of the obtained acrylic acid aqueous solution was fed to the water separation tower (300). Herein, the acrylic acid aqueous solution discharged from the (meth)acrylic acid absorption tower (100) was introduced into the 14$^{th}$ stage from the upper part of the water separation tower (300) at a flow rate of about 6.5 g/min.

The toluene reflux flow of the upper part of the water separation tower (300) was introduced into the first stage that is the uppermost stage at a flow rate of 11.95 g/min. Heat was fed through a reboiler at the lower part of the water separation tower (300) so that the temperature of the 16$^{th}$ stage became about 88 t or more, and the temperature of the 12nd stage may not exceed about 65° C.

After stable operation was conducted for about 10 hours, at a steady state, distillate was discharged to the upper part of the water separation tower (300) at a flow rate of about 14.14 g/min, and acrylic acid flow of about 4.31 g/min was obtained from the lower part of the water separation tower (300). Herein, at a steady state, the temperature of the upper part of the water separation tower (300) was maintained at about 40.4° C., and the temperature of the lower part was maintained at about 97.1° C.

As a result of operation of the water separation tower (300), the removal rate of water and acetic acid included in the acrylic acid extract and the acrylic acid aqueous solution fed to the water separation tower was about 99% or more, acrylic acid flow wherein most of water and acetic acid were removed could be obtained from the lower part of the water separation tower, and acrylic acid lost to the upper part of the water separation tower was about 0.13 wt %.

When the water separation tower (300) was operated for 5 days, production of polymer was observed at the stages around the feed stage in the tower, and after operated for 10 days, normal operation could not be conducted any longer due to the production of polymer in the tower.

The following Table 3 shows the flow rate and the concentration of each flow at steady stage operation of the water separation tower (300).

TABLE 3

|  |  | Acrylic acid aqueous solution | Reflux flow of azeotropic solvent | Upper flow of water separation tower | Lower flow of water separation tower |
|---|---|---|---|---|---|
| Mass Flow (g/min) |  | 6.50 | 11.95 | 14.14 | 4.31 |
| Composition (wt %) | Toluene | 0.00 | 99.74 | 84.90 | 0.00 |
|  | Acrylic acid | 67.99 | 0.10 | 0.13 | 99.96 |
|  | Acetic acid | 2.00 | 0.16 | 1.01 | 0.02 |
|  | Water | 29.99 | 0.00 | 13.96 | 0.00 |
|  | Heavies | 0.02 | 0.00 | 0.00 | 0.02 |

The treatment amount of the acrylic acid aqueous solution through the (meth)acrylic acid absorption tower (100) and water separation tower (300) was about 6.5 g per minute, production amount of acrylic acid was about 4.31 g per minute, and total recovery rate of acrylic acid was about 99.8%. As a result of calculating energy consumption amount using an ASPEN PLUS process simulator program (AspenTech Inc.), it was confirmed that 30.32 cal was consumed per 1 g of the obtained acrylic acid.

Comparative Example 2

Sequentially Passing Through [Acrylic Acid Absorption Tower—Extraction Tower—Water Separation Tower]

An acrylic acid aqueous solution was obtained from the (meth)acrylic acid absorption tower (100) by the same method as Example 1. The total amount of the obtained acrylic acid aqueous solution was fed to the (meth)acrylic acid extraction tower (200), and the acrylic acid extract discharged from the (meth)acrylic acid extraction tower (200) was fed to the water separation tower (300).

Herein, feed to the water separation tower (300) was only the acrylic acid extract, and the acrylic acid extract was introduced into the 14$^{th}$ stage from the upper part of the water separation tower (300) at a flow rate of about 8.3 g/min.

The toluene reflux flow of the upper part of the water separation tower (300) was introduced into the first stage that is the uppermost stage at a flow rate of about 8.4 g/min as a solvent. This corresponds to a reflux ratio (that is, the ratio of the flow rate of reflux liquid to discharged liquid) of about 1.5.

Heat was supplied through a reboiler at the lower part of the water separation tower (300) so that the temperature of the 16$^{th}$ stage became about 88° C. or more, and the temperature of the 12nd stage may not exceed about 65° C.

After stable operation was conducted for about 10 hours, at a steady state, distillate was discharged to the upper part of the water separation tower (300) at a flow rate of about 14.10 g/min, and acrylic acid flow of about 2.65 g/min was obtained from the lower part of the water separation tower (300). Herein, at a steady state, the temperature of the upper part of the water separation tower (300) was maintained at about 41.2° C., and the temperature of the lower part was maintained at about 96.5° C.

As the result of operation of the water separation tower (300), the removal rate of water and acetic acid included in the acrylic acid extract and the acrylic acid aqueous solution supplied to the water separation tower was about 99% or more, acrylic acid flow wherein most of water and acetic acid were removed could be obtained from the lower part of the water separation tower, and acrylic acid lost to the upper part of the water separation tower was about 1.07 wt %.

The water separation tower (300) could be operated stably without producing a polymer in the tower even after 10 days of long term operation.

The following Table 4 shows the flow rate and the concentration of each flow at steady stage operation of the water separation tower (300).

TABLE 4

|   |   | Acrylic acid aqueous solution | Reflux flow of azeotropic solvent | Upper flow of water separation tower | Lower flow of water separation tower |
|---|---|---|---|---|---|
| Mass Flow (g/min) | | 8.30 | 8.40 | 14.10 | 2.65 |
| Composition (wt %) | Toluene | 64.87 | 99.74 | 92.03 | 0.00 |
| | Acrylic acid | 32.90 | 0.10 | 1.07 | 99.92 |
| | Acetic acid | 0.66 | 0.16 | 1.24 | 0.02 |
| | Water | 1.55 | 0.00 | 5.66 | 0.00 |
| | Heavies | 0.02 | 0.00 | 0.00 | 0.06 |

The treatment amount of the acrylic acid aqueous solution through this process was about 4.15 g per minute, production amount of acrylic acid was about 2.65 g per minute, and total recovery rate of acrylic acid was about 94.8%. As a result of calculating energy consumption amount using an ASPEN PLUS process simulator program (AspenTech Inc.), it was confirmed that 54.25 cal were consumed per 1 g of the obtained acrylic acid.

DISCUSSION

As can be seen from the operation results of Examples 1-2 and Comparative Examples 1-2, according to the method of Example 1, there was a 7.6 cal decrease per 1 g of the recovered acrylic acid compared to the method of Comparative Example 1, which corresponds to energy reduction of about 25.1%. Further, according to the method of Example 2, there was a decrease of about 11.62 cal per 1 g of the recovered acrylic acid compared to Comparative Example 1, which corresponds to energy reduction of about 38.3%.

According to the method of Example 1, there was a decrease of about 31.52 cal per 1 g of the recovered acrylic acid compared to Comparative Example 2, which corresponds to energy reduction of 58.1%. Further, according to the method of Example 2, there was a decrease of about 35.54 cal per 1 g of the recovered acrylic acid compared to Comparative Example 2, which corresponds to energy reduction of about 65.5%.

As such, it is confirmed that the method of continuous recovery of (meth)acrylic acid according to the present invention may maintain a recovery rate of (meth)acrylic acid equivalent to the previous recovery method using a single water separation tower (the method of the comparative example), and yet may largely reduce energy consumption amount.

Moreover, if a distillation apparatus having equivalent capacity is used and equivalent amounts of azeotropic solvents and operation energy are introduced, the method according to the present invention may further increase treatment capacity of a (meth)acrylic acid aqueous solution, and recover (meth)acrylic acid with high energy efficiency. Furthermore, the method according to the present invention may maintain a low temperature around a feed stage of a water separation tower which has a relatively high possibility to produce a polymer of (meth)acrylic acid, and thus is effective for preventing production of a polymer, thereby providing more improved operation stability.

DESCRIPTION OF REFERENCE NUMERALS AND SIGNS

1: (meth)acrylic acid containing mixed gas
100: (meth)acrylic acid absorption tower
102, 103: (meth)acrylic acid aqueous solution transfer lines
150: acetic acid absorption tower
200: (meth)acrylic acid extraction tower
203: (meth)acrylic acid extract transfer line
300: water separation tower
350: phase separator
400: high boiling point by-product separation tower

The invention claimed is:

1. A method of continuous recovery of (meth)acrylic acid, comprising:
   contacting a mixed gas comprising (meth)acrylic acid, organic by-products, and vapor, which is produced by a synthesis reaction of (meth)acrylic acid, with water in a (meth)acrylic acid absorption tower (100) to obtain a (meth)acrylic acid aqueous solution;
   dividing and feeding the (meth)acrylic acid aqueous solution to a (meth)acrylic acid extraction tower (200) and a water separation tower (300);
   obtaining a (meth)acrylic acid extract with reduced water content from the (meth)acrylic acid aqueous solution that is fed to the (meth)acrylic acid extraction tower (200), and feeding it to a water separation tower (300); and
   distilling the (meth)acrylic acid aqueous solution and the (meth)acrylic acid extract that are fed to the water separation tower (300) to obtain (meth)acrylic acid.

2. The method for continuous recovery of (meth)acrylic acid according to claim 1, wherein 5~70 wt % of the (meth)acrylic acid aqueous solution obtained in the (meth)acrylic acid absorption tower (100) is fed to the (meth)acrylic acid extraction tower (200), and the remainder is fed to the water separation tower (300).

3. The method for continuous recovery of (meth)acrylic acid according to claim 1, wherein the synthesis reaction of (meth)acrylic acid is an oxidation reaction of at least one compound selected from the group consisting of propane, propylene, butane, isobutylene, t-butylene, and (meth)acrolein in the presence of a gas phase catalyst.

4. The method for continuous recovery of (meth)acrylic acid according to claim 1, wherein the internal temperature of the (meth)acrylic acid absorption tower (100) is maintained at 50 to 100° C.

5. The method for continuous recovery of (meth)acrylic acid according to claim 1, wherein in the step of obtaining the (meth)acrylic acid aqueous solution, a (meth)acrylic acid aqueous solution is discharged to the lower part of the (meth)acrylic acid absorption tower (100), and (meth)acrylic acid-stripped non-condensable gas is discharged to the upper part of the (meth)acrylic acid absorption tower (100).

6. The method for continuous recovery of (meth)acrylic acid according to claim 5, further comprising contacting the non-condensable gas with water to recover acetic acid that is included in the non-condensable gas.

7. The method for continuous recovery of (meth)acrylic acid according to claim 1, wherein the water fed to the (meth)acrylic acid absorption tower (100) includes organic by-products at a concentration of 3 to 20 wt %.

8. The method for continuous recovery of (meth)acrylic acid according to claim 1, wherein the (meth)acrylic acid aqueous solution obtained in the (meth)acrylic acid absorption tower (100) includes (meth)acrylic acid at a concentration of 40 to 90 wt %.

9. The method for continuous recovery of (meth)acrylic acid according to claim 1, wherein the (meth)acrylic acid extract is obtained by contacting the (meth)acrylic acid aqueous solution that is fed to the (meth)acrylic acid extraction tower (200) with a hydrophobic extraction solvent to remove water included in the aqueous solution.

10. The method for continuous recovery of (meth)acrylic acid according to claim 9, wherein the hydrophobic extraction solvent is at least one selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

11. The method for continuous recovery of (meth)acrylic acid according to claim 9, wherein the (meth)acrylic acid extract is obtained from the upper part of the (meth)acrylic acid extraction tower (200) and fed to the water separation tower (300), and
at least a part of the lower discharged liquid of the (meth)acrylic acid extraction tower (200) is fed to the upper end of the (meth)acrylic acid absorption tower (100) and used as an absorption solvent of (meth)acrylic acid.

12. The method for continuous recovery of (meth)acrylic acid according to claim 11, wherein the lower discharged liquid of the (meth)acrylic acid extraction tower (200) includes (meth)acrylic acid at a concentration of 5 wt % or less.

13. The method for continuous recovery of (meth)acrylic acid according to claim 11, wherein the upper end of the (meth)acrylic acid absorption tower (100) to which at least a part of the lower discharged liquid of the (meth)acrylic acid absorption tower (200) is fed is at least one point corresponding to a height of 70% or more from the lowest part of the absorption tower.

14. The method for continuous recovery of (meth)acrylic acid according to claim 1, wherein the distillation in the water separation tower (300) is conducted in the presence of a hydrophobic azeotropic solvent.

15. The method for continuous recovery of (meth)acrylic acid according to claim 14, wherein the hydrophobic azeotropic solvent is at least one selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

16. The method for continuous recovery of (meth)acrylic acid according to claim 15, wherein the hydrophobic azeotropic solvent includes the same compound as the hydrophobic extraction solvent in the (meth)acrylic acid extraction tower (200).

17. The method for continuous recovery of (meth)acrylic acid according to claim 14, wherein discharged liquid including (meth)acrylic acid is recovered from the lower part of the water separation tower (300), and discharged liquid including a hydrophobic azeotropic solvent, water, and acetic acid is recovered from the upper part of the water separation tower (300), by distillation in the water separation tower (300).

18. The method for continuous recovery of (meth)acrylic acid according to claim 17, wherein the upper discharged liquid of the water separation tower (300) is separated into an organic layer including the hydrophobic azeotropic solvent and an aqueous layer including acetic acid, at least a part of the organic layer is fed to the upper end of the water separation tower (300) as an azeotropic solvent, and at least a part of the aqueous layer is fed to the upper end of the (meth)acrylic acid absorption tower (100) as an absorption solvent.

* * * * *